United States Patent [19]

Uffenhiemer et al.

[11] Patent Number: 5,133,218
[45] Date of Patent: Jul. 28, 1992

[54] SAMPLE LIQUID ASPIRATING AND DISPENSING PROBE

[75] Inventors: Kenneth F. Uffenhiemer, Mahopac; Nicholas F. Di Domenico, Pine Bush, both of N.Y.

[73] Assignee: Tritech Partners, Tarrytown, N.Y.

[21] Appl. No.: 685,983

[22] Filed: Apr. 15, 1991

Related U.S. Application Data

[63] Continuation of Ser. No. 384,649, Jul. 24, 1989, abandoned.

[51] Int. Cl.⁵ ............................................. G01N 1/14
[52] U.S. Cl. ................................................. 73/864.14
[58] Field of Search ........... 73/864.01, 864.11, 864.12, 73/864.14–864.18, 864.21–864.25, 864.73, 866.5; 422/100; 138/155; 285/334.5, 328

[56] References Cited

U.S. PATENT DOCUMENTS

| | | | |
|---|---|---|---|
| 448,717 | 3/1891 | Hogan | 285/334.5 |
| 1,348,667 | 8/1920 | Snyder | 285/328 |
| 2,660,342 | 11/1953 | Ruf | 73/864.18 |
| 3,175,734 | 3/1965 | Heiss | 73/864.14 |
| 3,401,564 | 9/1968 | Hrdina | 73/864.21 |
| 3,754,687 | 8/1973 | Norton | 73/864.14 |
| 3,830,108 | 8/1974 | Spong | 73/864.14 |
| 3,873,274 | 3/1975 | Neisius | 73/864.16 |
| 4,121,466 | 10/1978 | Reichler et al. | 73/864.22 |
| 4,586,546 | 5/1986 | Mezei et al. | 73/864.24 |

FOREIGN PATENT DOCUMENTS

| | | | |
|---|---|---|---|
| 2815023 | 10/1979 | Fed. Rep. of Germany | 422/100 |
| 6606343 | 11/1966 | Netherlands | 73/864.14 |

Primary Examiner—Robert Raevis
Attorney, Agent, or Firm—Jeffrey M. Greenman; James J. Romano, Jr.

[57] ABSTRACT

The sample liquids analysis system includes a probe which is automatically operable to successively aspirate sample liquids and reagent and/or other sample liquids processing liquids and to dispense the same in turn into sample liquids analysis apparatus for automatic, successive sample liquids analyses. Isolation liquid supply apparatus are operatively associated with the sample liquids aspirating the dispensing probe and operate to introduce an isolation liquid which is immiscible with the sample liquids and which selectively wets the probe to the substantial exclusion of the sample liquids, to the probe to, in combination with operatively associated rinse liquid supply apparatus which operate to fill the probe with a rinse liquid between successive sample liquids aspirations, reduce sample liquids carryover to ultra low levels. The sample liquids aspirating and dispensing probe are operated by the rinse liquid supply apparatus; and comprise a probe body member, and an active probe component operatively connected thereto by a readily disconnectable connector, thus making possible the ready and convenient replacement of the active probe component without adverse effect upon the essential configuration and/or operational characteristics of the rinse liquid supply apparatus, and thereby upon the overall performance of the sample liquids analysis system. The configuration of the probe operates to reduce sample liquids flow velocity in the active probe component, thereby further reducing sample liquids carryover.

9 Claims, 8 Drawing Sheets

SAMPLE LIQUID ASPIRATING AND DISPENSING PROBE

BACKGROUND OF THE INVENTION:

1. Field of The Invention

This invention relates to new and improved apparatus and method for the automated analysis of successive sample liquids with ultra low sample liquid carryover therebetween to maximize the accuracy of the sample liquids analysis results, and to new and improved sample liquid aspirating and dispensing probe for use therein.

2. Description of the prior art

Although apparatus and method for the highly effective automated analysis of successive sample liquids which bear a number of significant similarities to those disclosed herein are disclosed in U.S. Pat. No. 4,629,703 issued Dec. 16, 1986 to Kenneth F. Uffenhiemer for "Automated Analytical System" and assigned to Technicon Instruments Corporation, Tarrytown, New York, those significant similarities do not include the provision for ultra low carryover between successive sample liquids as made possible by the apparatus and method of this invention.

Although successive sample liquids aspirating and/or dispensing probe means which are highly effective to that task with very low sample liquid carryover are disclosed in U.S. Pat. No. 4,121,466 issued Oct. 24, 1978 to Allen Reichley et al, for "Liquid Dispenser With An Improved Probe" and assigned to Technicon Instruments Corporation, it may be understood that the same, which rely solely on an isolation liquid which is immiscible with the sample liquids and which selectively wets the relevant probe walls to the substantial exclusion of the sample liquids to minimize sample liquid carryover, and which specifically rules out the utilization of a rinse liquid in combination with that isolation liquid to rinse the relevant probe walls, simply cannot provide the ultra low sample liquid carryover as provided by the apparatus and method of this invention. In addition, and although the probe means are only depicted schematically in U.S. Pat. No. 4,121,466, it is nonetheless clear that the same are totally distinct in structural configuration from those of this invention.

The respective disclosures of U.S. Pat. Nos. 4,629,703 and 4,121,466 are hereby incorporated by reference in this specification.

OBJECTS OF THE INVENTION

It is, accordingly, an object of the invention to provide new and improved apparatus and method for the automated analysis of successive sample liquids with ultra low sample liquid carryover therebetween, to thereby maximize the accuracy of the successive sample liquids analysis results.

It is another object of the invention to provide new and improved sample liquid aspirating and dispensing probe means for use in that sample liquids analysis system.

It is another object of the invention to provide new and improved successive sample liquids analysis apparatus and method as above which are operable at high sample liquid analyses rates.

It is another object of the invention to provide new and improved successive sample liquids analysis apparatus and method as above which are immediately applicable, without modification, to a wide variety of different sample liquids analyses with regard to different sample liquids analytes of interest.

It is another object of the invention to provide new and improved successive sample liquids analysis apparatus as above which are of generally straightforward configuration and manner(s) of operation, and which require the use of only readily available components and materials of proven effectiveness and dependability to the task at hand in the fabrication thereof.

It is another object of the invention to provide new and improved sample liquid aspirating and dispensing probe means as above which are of particularly simple and inexpensive configuration, and which include an active probe means component which may be readily and conveniently replaced in the event of damage at minimal cost with minimal sample liquids analysis system down-time, and with virtually no adverse effect on the accuracy of subsequent analysis system performance.

It is a further object of the invention to provide new and improved successive sample liquids analysis system and method as above which are particularly, but not exclusively, adapted to the automated performance of non-isotopic immunoassay on human blood sera sample liquids with regard to a broad range of sample liquid analytes, and wherein the ultra low sample liquid carryover provided by the apparatus and method of the invention is a requirement to the accuracy and validity of the immunoassay results.

SUMMARY OF THE DISCLOSURE

As disclosed herein, the new and improved successive sample liquids analysis system of the invention comprises supply means which are operable to successively aspirate sample liquids from operatively associated sample liquids supply means, and dispense the same in turn, along with aspirated sample liquids reagent(s) and/or processing liquids, into operatively associated automated sample liquids analysis means for successive sample liquids analyses. Isolation liquid supply means are operatively associated with the probe means, and are operable to coat the relevant interior and exterior wall surfaces of the same with a layer of an isolation liquid which is immiscible with the sample liquids, and which preferentially wets those probe means wall surfaces to the substantial exclusion of the sample liquids. Rinse liquid supply means are also operatively associated with the probe means, and are operable to flow a rinse liquid therethrough to rinse the isolation liquid layer following sample liquid aspiration in each instance, and to leave the probe means substantially filled with rinse liquid following sample liquid dispensing in each instance; thereby, in combination with the isolation liquid, reducing sample liquid carryover to the ultra low levels required for contemporary, highly sophisticated, automated clinical sample liquids analyses. For use of the sample liquids analysis system in applications wherein relatively large volumes of the sample liquids are aspirated and dispensed by the probe means, the invention further includes aspiration of an appropriate surfactant liquid for mixture with the sample liquids in the probe means; and this functions to better retain the integrity of the sample liquids in the probe means to even further reduce sample liquid carryover.

As disclosed herein, the new and improved probe means of the invention include rinse liquid supply conduit means, which also function to aspirate and dispense sample liquids, operatively connected thereto; and the probe means comprise a probe body member, a active probe component, and connecting means operable to connect the conduit means and the active probe component within the probe body member to place the same in fluid flow communication. The connecting means are readily disconnectable to make possible the ready and convenient replacement of the active probe component in the probe means without adverse effect upon the configuration and/or operational characteristics of the rinse liquid supply conduit, and thereby upon overall analysis system performance. The active probe component comprises a tubular body member having first and second body member portions, with the first of said body member portions being of larger diameter than the second of the same and transitioning smoothly thereinto; and this also functions to reduce sample liquid carryover by reducing the flow velocity of sample liquids in the first of said active probe component body member portions.

DESCRIPTION OF THE DRAWINGS

The above and other significant objects and advantages of our invention are believed made clear by the following detailed description thereof taken in conjunction with the accompanying drawings wherein.

DETAILED DESCRIPTION OF THE INVENTION

Figure 1:
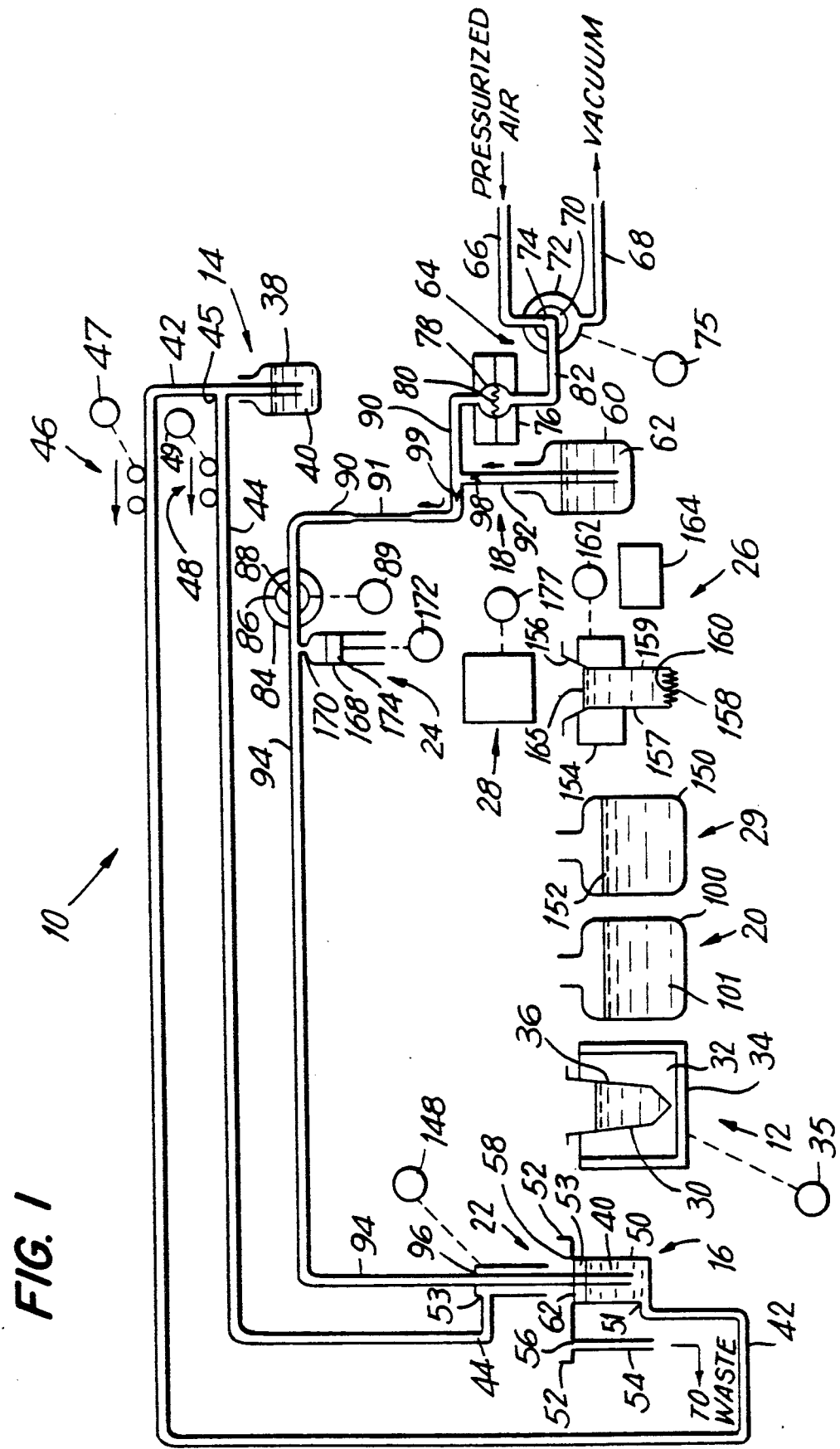
FIG. 1 is generally schematic view of an automated sample liquids analysis system representatively configured and operable in accordance with the teachings of the currently contemplated best mode of the apparatus and method of the invention.

Referring now to FIG. 1 of the application drawings, an automated, successive sample liquids analysis system representatively configured and operable in accordance with the currently contemplated best mode of the apparatus and method of our invention is depicted schematically and indicated generally at 10.

The sample liquids analysis system 10 comprises sample liquid supply means as indicated generally at 12, immiscible isolation liquid supply and reservoir means as indicated generally at 14 and 16, respectively, rinse liquid supply means as indicated generally at 18, bufferdilutent liquid supply means as indicated generally at 20, sample liquid aspirating and dispensing probe means as indicated generally at 22, sample liquid pump means as indicated generally at 24, and sample liquid reaction and analysis means as indicated generally at 26, respectively. In addition, reagent and/or substrate liquid(s) supply and dispensing means for the addition thereof to the sample liquids in the sample liquid reaction and analysis means for mixture and reaction therewith as required for sample liquids analysis, are indicated generally at 28; while supply means for an agent or agents) as may be required in addition to the reagent and/or substrate liquid(s) for sample liquids reaction and analysis are depicted schematically and indicated generally at 29 in FIG. 1.

As generally described, it will be readily understood by those skilled in the automated sample liquids analysis art that the sample liquids analysis system 10 is operable to successively supply, react and quantitively analyze each of a series of sample liquids in turn with regard to one or more analytes of interest contained therein; with a major emphasis regarding system 10 being on the reduction of sample liquid carryover, i.e. the contamination of a succeeding sample liquid by the residue of a preceding sample liquid, to heretofore virtually unattainable, ultra low levels commensurate with the exceedingly stringent accuracy requirements of highly sophisticated and specialized contemporary clinical chemistries, for example those involved in non-isotopic immunoassays on human blood sera.

As more specifically described, sample liquid means preferably take the general form of those disclosed in each of U.S. Pat. Nos. 4,099,921, 4,115,861 and 4,168,955, resepectively for "Clinical Analyzer" issued Jul. 11, 1978, Nov. 7, 1978 and Sept. 25, 1979 to Robert W. Allington, and assigned to instrumentation Specialties Company; and the respective disclosures of those United States Patents are hereby incorporated by reference in this disclosure.

To the above effect, the sample liquids supply means 12 comprise a plurality of like sample liquid receptacles, for example 78 in number, which are respectively operatively disposed in groups in a plurality of moveable shuttles, one of which is shown at 32 in FIG. 1. The shuttles 32 are in turn supported in and moveable by a shuttle support mechanism as indicated at 34, driven in turn by electric drive motor means as indicated schematically at 35 in FIG. 1; with the mechanism 34 operating to support and peridically move the shuttles 32 in such manner that the sample liquid receptacles 30, each of which contains a quantity of a sample liquid to be analyzed as indicated at 36 in FIG. 1, are indexed in turn to a sample liquid off-take station relative to probe means 22, and retained thereat for precisely the same period of time for the aspiration of precisely the same volume of sample liquid therefrom by the probe means 22 in each instance.

The isolation liquid supply means 14 comprise a container 38 of an appropriate isolation liquid as indicated at 40, and which is immiscible with the sample liquids 36. Readily compressible isolation liquid supply conduits 42 and 44, which branch as indicated at 45, respectively extend as shown in FIG. 1 from container 38 to isolation liquid reservoir means 16 and probe means 22; and pump means, for example peristaltic pumps as schematically indicated at 46 and 48, and which are particularly suitable for precise isolation liquid pumping at low flow rates as discussed in greater detail hereinbelow, are respectively operatively formed as shown with the relevant portions of compressible isolation liquid supply conduits 42 and 44. The peristaltic pumps 46 and 48 are driven in turn as indicated in FIG. 1 by electric drive motor means as schematically indicated at 47 and 49; and are operable when so driven to supply the isolation liquid 40 in respectively precisely controlled quantities along those conduits from isolation liquid supply container 38 to isolation liquid inlets 51 and 53 of the isolation liquid reservoir means 16 and probe means 22, respectively.

Although by now believed to be well understood by those skilled in this art, it is here reiterated to insure completeness of this disclosure that for use, for example, with essentially aqueous sample liquids 36, and an active component of probe means 22 of an appropriately hydrophobic material, for example Teflon as described in detail hereinbelow, the isolation liquid 40 would be constituted, for example, by an appropriately hydrophobic fluorinated or per-fluorinated hydrocarbon liquid, or "oil" as the same has come to be termed in the sample liquids analysis art, which is preferentially attracted to and selectively "wets" that active probe means component to the substantial exclusion of the essentially aqueous sample liquids 36, which are immiscible therewith; thereby substantially preventing the adherence of sample liquid residue to that active probe component. This in turn minimizes sample liquid carryover on the active probe means component, with attendant increase in the accuracy of the sample liquids analysis results This phenomenon of selective wettability and the application thereof to sample liquids analysis for minimization of sample liquid carryover through use of an appropriate isolation liquid, is disclosed in some detail in each of U.S. Pat. No. 4,602,995 issued Jul. 29, 1986 to Michael M. Cassaday, et al, for "Liquid Level Adjusting And Filtering Device," U.S. Pat. No. 4,515,753 issued May 7, 1985 to John L. Smith, Ph.D., et al, for "Integral Reagent Dispenser," and U.S. Pat. No. 4,678,641 issued Jul. 7, 1987 to Michael M. Cassaday, et al, for "Isolation Liquid Layer Retention Device," all assigned to Technicon Instruments Corporation of Tarrytown, New York; and the respective disclosures of each of those United States Patents are hereby incorporated by reference in this specification.

The isolation liquid reservoir reservoir means 16 comprise an open topped, generally cylindrical reservoir body member 50 fabricated for example from an appropriately hydrophobic plastic material by molding, which is supplied as shown in FIG. 1 at inlet 51 at the bottom of the body member with isolation liquid 40 from container 38 by peristaltic pump 46 via supply conduit 42 as discussed hereinabove. An enlarged liquid overflow chamber 52 is formed as shown at the top of the reservoir body member 50, and comprises a drain conduit 54 extending downwardly therefrom as indicated to waste; it being noted that the level 56 of the upper end of the drain conduit 54 is coincident with the level 58 of the top of the reservoir body member 50, whereby the liquid level in the reservoir means 16 will be maintained coincident therewith, with any excess liquidflowing therefrom to waste via drain conduit 54.

The rinse liquid supply means 18 comprise a container 60 of any suitable rinse liquid, for example distilled water, as indicated at 62 in FIG. 1. Rinse liquid supply pump and pump drive means are indicated generally at 64, and comprise pressurized air and vacuum supply conduits 66 and 68 which respectively extend as shown from non-illustrated sources thereof to the rotatable body member 70 of a three-way valve 72, including valve passage 74. Rotatable valve body member 70 is driven as shown by electric drive motor means, for example a solenoid, as indicated schematically at 75 in FIG. 1.

A diaphragm pump is indicated at 76, and includes a pumping chamber 78 divided as shown by a diaphragm 80; and a conduit 82 extends as shown in FIG. 1 to connect valve passage 74 of valve 72 with one side of pumping chamber 78. A two-way rinse liquid supply valve is indicated at 84, and includes a rotatable valve body member 86 having a valve passage 88 extending therethrough. Valve body member is driven as shown by electric drive motor means, again for example a solenoid, as indicated at 89. A conduit 90 extends as shown to connect the other side of pumping chamber 78 with one side of rinse supply valve 84. A conduit 92 branches as shown from conduit 90 to extend into the supply of rinse liquid 62 in container 60; while a flexible conduit 94 extends as shown to connect the other side of valve 84 to the rinse liquid inlet 96 of the probe means 22. Check valves as indicated at 98 and 99 are provided in conduits 90 and 92 to restrict rinse liquid flow therein to the indicated directions; while conduit 90 comprises a flow restrictor tube section 91 which restricts rinse liquid flow therethrough to levels which will not degrade the effectiveness of the isolation liquid in minimizing sample liquid carryover in the probe means 22 as discussed in greater detail hereinbelow.

For operation of the rinse liquid supply means 18 to supply rinse liquid 62 from container 60 to the rinse liquid inlet 96 of the probe means 22, and with the body member 86 of two-way valve 84 rotated to the "open" position thereof of FIG. 1 to connect conduits 90 and 94, it will be clear that cycling of the rotatable valve body member 70 of three-way valve 72 between the depicted position thereof wherein valve passage 74 connects conduits 66 and 82, and the non-illustrated position thereof wherein passage 74 connects conduits 68 and 82, respectively, will drive pump diaphragm 80 to pump the rinse liquid 62 from container 60 via conduits 92, 90 and 94 for supply to the rinse liquid inlet 96 of the probe means 22.

The buffer-diluent liquid supply means 20 comprise an open-topped container 100 of the buffer-diluent liquid, for example distilled water, as indicated at 101 in FIG. 1. For certain applications of the analysis system 10 of our invention, as dictated in part by the volumes of the sample liquids 36 to be aspirated by the probe means 22, the buffer-diluent liquid 10 may include a predetermined quantity by volume, for example 20%, of an appropriate surfactant, for example that readily available under the Trademark "Triton X-100," which operates in conjunction with the isolation liquid 40 and the rinse liquid 62 to even further reduce sample liquids carryover to the requisite ultra low levels as discussed in greater detail hereinbelow.

Figure 2:
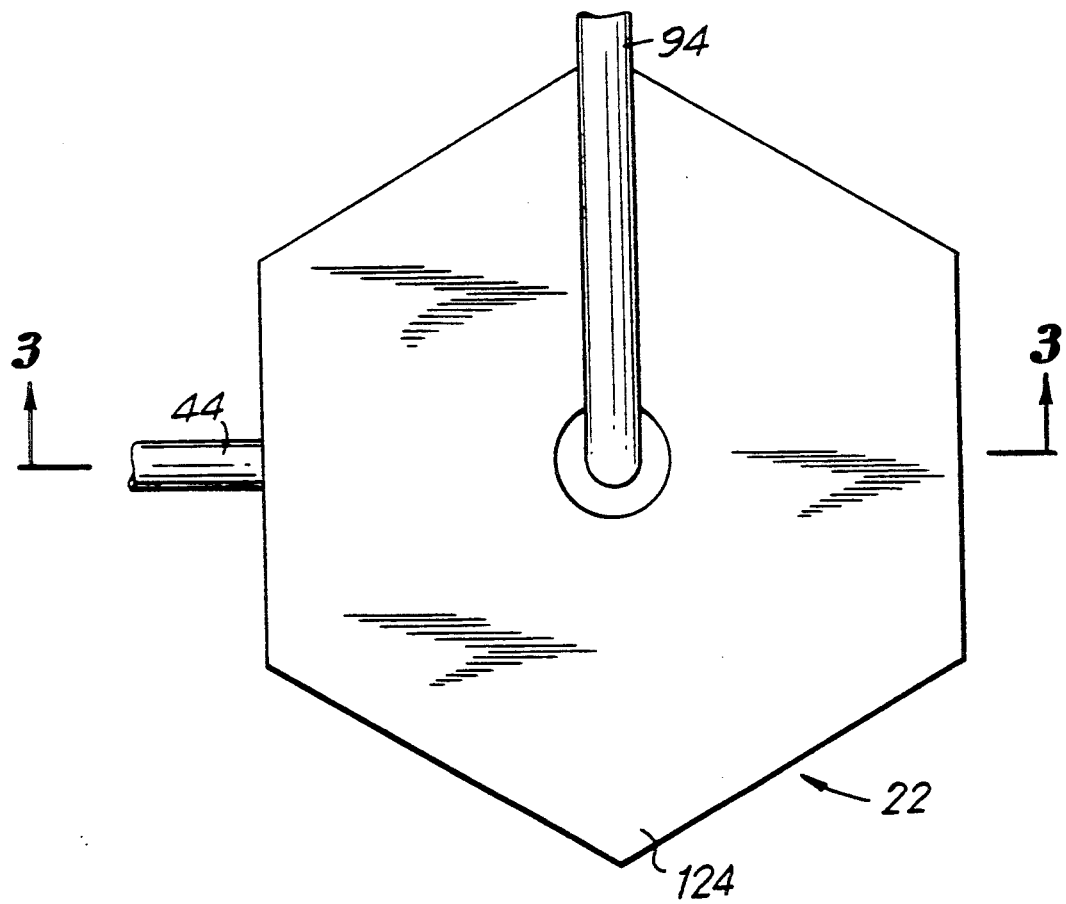
FIG. 2 is a top plan view of the sample liquid aspirating and dispensing probe means of the system of FIG. 1.
Figure 3:
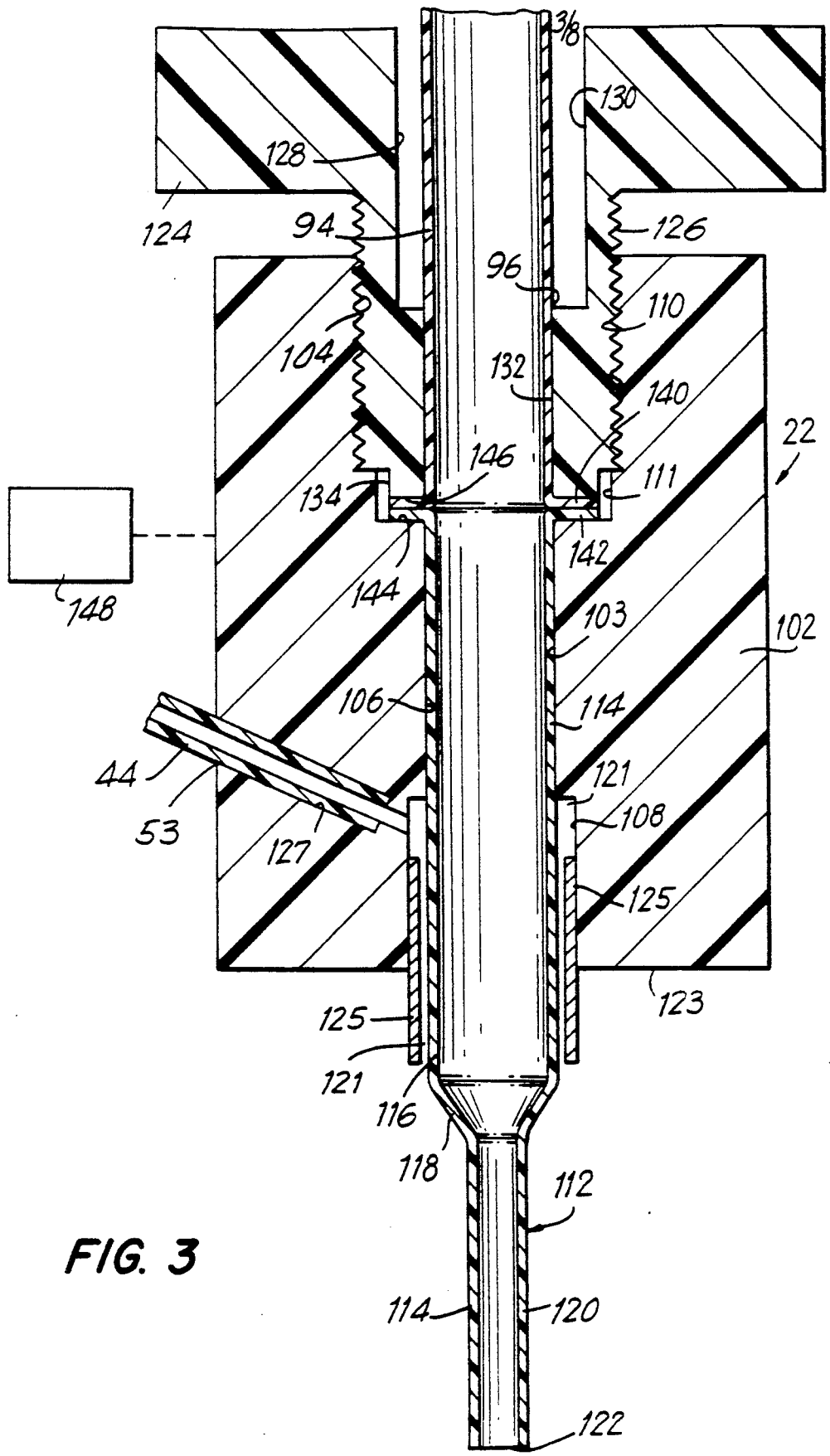
FIG. 3 is a cross-sectional view taken essentially along line 3—3 in FIG. 2.

With reference now to FIGS. 1, 2 and 3 of the application drawings for more detailed description of the probe means 22 the same will be seen to comprise a generally cylindrical body member 102 having a stepped, generally axial bore 103 extending therethrough, and comprising axially aligned bore sections 104, 106 and 108 as best seen in FIG. 3. Bore section 104 is threaded as indicated at 110 almost to the inner end thereof, leaving an unthreaded bore section 111 of relatively small axial extent at that inner bore end.

The active probe component is indicated generally at 112 in FIG. 3, and comprises a generally pipette-like body member 114 having a tubular upper body portion 116 which smoothly transitions or "necks down" as shown at 118 to a lower tubular body portion 120 which extends from the probe body member 102 well below the lower surface 123 thereof to terminated in an open tip 122. This configuration of the probe component 112 of course provides for a greater probe component volume per unit length for upper probe body portion 116 than for lower probe body portion 120; and, for a constant liquid flow rate into the probe component 112 through open tip 122, will in turn provide for a lower liquid flow velocity through the upper probe body portion 116 than through the lower probe body portion 120.

The active probe component 112 is operatively disposed in the body member bore 103 concentrically thereof, with the outer wall of upper probe component body portion 116 being in firm surface contact with the wall of bore section 106 to prevent radial movement of the probe component 112 relative to probe body member 102; and the probe component 112 extends as shown through body member bore section 108 with wall clearance to provide an annulus as indicated at 121 therebetween to completely surround the relevant wall surfaces of the upper probe component body portion 116 which extends therethrough.

A length of tubing of a material of appropriate strength characteristics is indicated at 125 in FIG. 3, and is disposed as shown, for example by press-fitting, in body member bore portion 108 to extend therefrom and surround upper probe component portion 116, both within annulus 121 and for some distance below the lower surface 123 of probe body member 102, essentially for preventing excessive radial movement of the relevant portion of the active probe component 112 relative to the body member 102, and to provide some measure of protection against impact damage to the same.

A generally radially, downwardly extending stepped bore is indicated at 127 in FIG. 3, and extends as shown through the probe body member 102 into fluid flow communication with the annulus 121; and the end portion of isolation liquid supply conduit 44 extends thereinto as shown, and is retained therein in any appropriate manner, for example by simple press-fitting, to thus place conduit 44 and annulus 121 in isolation liquid flow communication.

A hex nut is indicated at 124 in FIG. 3, and is threaded as shown at 126 for the screwing thereof into the complementally threaded probe body member bore portion 104. The hex nut 124 comprises a stepped bore 128 extending centrally thereof; and it will be clear that upon tightening of the hex nut 124 into the probe body member 102, the bores 128 and 103 will be in alignment as shown. Stepped hex nut bore 128 includes upper and lower portions 130 and 132, with the former being larger than the latter and the inner end of the hex nut 124 includes a relatively small unthreaded portion as indicated at 134 in FIG. 3.

For use, for example, with essentially aqueous sample liquids 36 and a hydrophobic isolation liquid 40 as discussed hereinabove, it may be understood that active probe component 112 is preferably fabricated, as by drawing, from an appropriate hydrophobic plastic material, for example essentially rigid Teflon; while, for all applications, probe body member 102 and hex nut 124 are preferably machined from a clear acrylic material and tubing length 125 cut to an appropriate length from a piece of stainless steel tubing of suitable diameter FIG. 3 makes clear that the rinse liquid supply conduit 94 extends through hex nut bore 128, and that the tubing wall is in firm surface contact with the wall of lower hex nut bore portion 132 to prevent radial movement therebetween; with conduit 94 terminating as shown in a flared end 140 within the unthreaded bore section portion 111 of probe member bore section 104. In like manner, upper probe component body portion 116, which is of the same inner and outer diameters as rinse supply conduit 94, also terminates in a flared end 142 in bore section portion 111; with flared ends 140 and 142 being of essentially the same diameter Assembly of the probe means 22 is readily accomplished by the simple press-fitting of tubular length 125 into probe means body member bore section 108 to the position thereof depicted in FIG. 3; the simple insertion and movement of active probe component 112 into and through the probe body member bore 103 from above the body member 102 until the component 112 comes to rest in the depicted position thereof with the flared component end 142 in firm contact with the lower surface 144 of bore section 104; the simple insertion and movement of rinse liquid supply conduit 94 into and through the hex nut bore 128 from below until the conduit comes to rest in the depicted position thereof with the flared conduit end 140 in firm contact with the bottom surface 146 of the hex nut 124; and the equally simple insertion and tightening of the hex nut 124 into the threaded body member bore section 104 to very firmly press the flared probe component and rinse supply conduit flared ends 142 and 140 together between opposed bore section and hex nut surfaces 144 and 146 as depicted in FIG. 3 to form an extremely fluid-tight juncture, or pressure fitting therebetween, and place the same in unrestricted fluid flow communication. The end portion of isolation liquid supply conduit 44 is then simply press-fitted into probe body member bore 127 to the position thereof depicted in FIG. 3 to complete the assembly of the probe means 22.

Electromechanically operable probe means drive means, including appropriate electric drive motor means, are indicated schematically at 148 in FIG. 3; and are mechanically connected as indicated by the dashed line to the probe means body member 102, and operable, in manner well understood by those skilled in this art, to index probe means 22 between respective operable positions thereof relative to same liquid supply means 12, isolation liquid supply means 16, buffer-diluent supply means 20 and, if required, agent(s) supply means 29, attendant the sample liquids analysis process, all as described in greater detail hereinbelow.

In the manner of buffer-diluent liquid supply means 20, the reaction agent(s) supply means 29 comprise an open-topped container 150 of such agent(s) as indicated at 152. For use, for example, of the sample liquids analysis system 10 in the performance of non-isotopic heterogeneous immunoassays on sample liquids 36 as constituted by human blood sera, a representative agent 152 in question would be magnetic particles, or magnetic solid phase, in suspension in an appropriate buffer-diluent liquid as discussed hereinabove.

The sample liquid reaction and analysis means 26 preferably take the form of those disclosed in U.S. Pat. No. 4,357,301 issued Nov. 2, 1982 to Michael M. Cassaday, et al, for "Reaction Cuvette," and assigned to Technicon Instruments Corporation, Tarrytown, New York; and the disclosure of that United States Patent is incorporated by reference herein. To that effect, the reaction and analysis means 26 comprise a circular reaction tray as schematically indicated at 154 in FIG. 3, and a circular array of individual, open-topped cup-like containers, or reactions cuvette , one of which is indicated at 156, supported adjacent the outer periphery thereof, and respectively including exposed, radially aligned transparent cuvette wall sections as indicated at 15 and 159. The reaction tray 154 and cuvettes are fabricated by molding from a appropriately chemically inert plastic material; and each of the reaction cuvettes 156 comprises a bottom surface 158 of a hydrophilic material having a plurality of upwardly extending ridges or projections as indicated at 160 formed thereon, and which function as described in detail in U.S. Pat. No. 4,357,301, to penetrate a film of the immiscible isolation liquid 40 which encapsulates the sample liquids 36 upon the dispensing thereof into the cuvettes 156 by probe means 22 to render the same physically accessible for mixture and reaction(s) as required with sample liquids analysis reagent(s) and/or agent(s) in the cuvettes. The reaction tray 154 is indexed by intermittent rotation, which may be sequentially bi-directional, by electromechanical tray drive means, including an electrical stepping motor as indicated schematically indicated at 162 in FIG.3, to present the reaction cuvettes in turn to respective sample and agent(s) liquids, and reagent(s) liquids dispensing stations, for the introduction of those liquids to the cuvette, and appropriate reactions therebetween; and finally therefrom to a sample liquids analysis or "read-out-38 station whereat sample liquids analysis means, for example an operatively associated colorimeter as schematically indicated at 164 in FIG. 3, are operable to automatically analyze the thusly reacted sample liquids, one of which is indicated at 165 in FIG. 3, with regard to the analyte(s) of interest through the transparent cuvette wall sections 157 and 159. Operation of an automated sample liquids analysis system through use of sample liquids reaction and analysis means 26 as described is disclosed in detail in U.S. Pat. No. 4,629,703 as incorporated by reference in this specification hereinabove.

The sample liquids pump means 24 preferably take the form of a very precisely operable syringe pump as indicated at 168 in FIG. 1, and which is connected as shown to rinse liquid supply conduit 94 by a branch conduit 170. Syringe pump is driven by an electric drive motor as schematically indicated at 172; and it will be clear that with rinse liquid supply valve rotated to the non-illustrated "closed" position thereof, downward movement of the syringe pump piston 174 will be operable to aspirate sample liquids 36 in very precisely predetermined quantities through the open tip 122 of probe component 112 (FIG. 3) into the probe component via the reduced pressure created thereby in the rinse liquid supply conduit 94.

Reagent and/or substrate liquids supply means 28 may take any form appropriate to the dispensing of the same into the reaction cuvettes 156 at the reagent (s) dispensing stations(s) as described hereinabove for mixing and reaction with the sample liquids 36 within the cuvettes 156 as required for sample liquids analyses. A such, these supply means may, for example, take the form of appropriately refrigerated trays or other support mechanisms of reagent and substrate liquids containers, for the reagent liquids for example the integral dispensers as disclosed in U.S. Pat. No. 4,515,753 incorporated by reference hereinabove, each with operatively associated dispensing probe means as disclosed in U.S. Pat. No. 4,121,466, incorporated by reference hereinabove, and respectively operable to dispense reagent and/or substrate liquid therefrom as required into the reaction cuvettes at the dispensing stations therefor of the reaction tray 154 as described hereinabove. The required electromechanical drive means for these operations of course include electric drive motor means as schematically indicated at 177 in FIG. 3.

Figure 4:
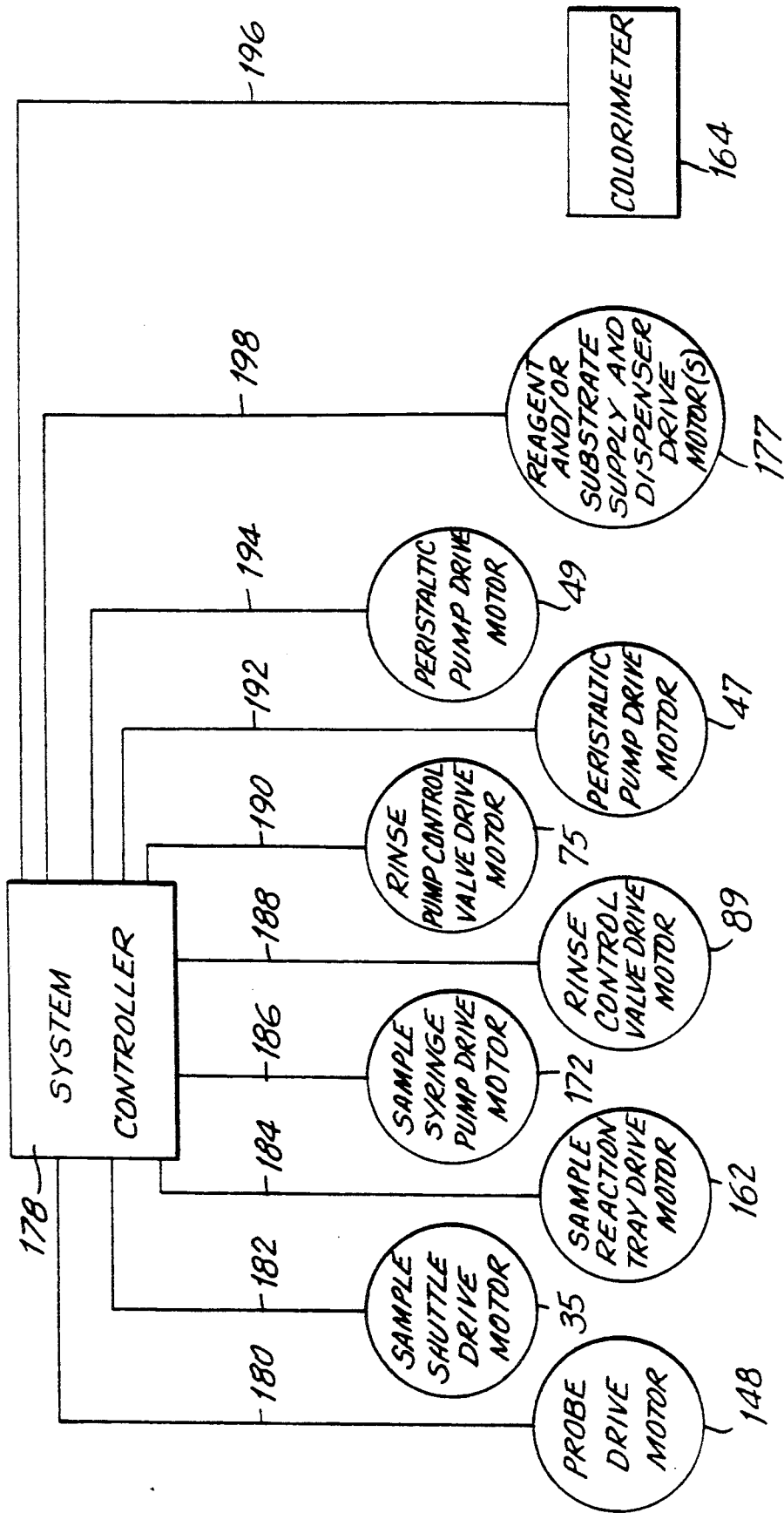
FIG. 4 is a schematic diagram of a representative control system for the sample liquids analysis system of FIG. 1.

FIG. 4 schematically depicts a representative control system for the automated sample liquids analysis system 10; and, to that effect, will be seen to include a system controller as indicated at 178 and taking, for example, the form of an appropriately programmable microprocessor device or "computer" as the same are more commonly termed. System controller 178 is electrically connected as indicated by lines 180, 182, 184 and 186 to probe means drive motor 148, sample supply shuttle means drive motor 35, sample reaction tray drive means drive motor 162 and sample syringe pump drive motor 172, resepectively; and system controller 178 is further electrically connected as indicated by lines 188, 190, 192 and 194 to rinse liquid control valve drive motor 89, rinse liquid pump control valve drive motor 75, and peristaltic pump drive motors 47 and 49, which may be combined into one drive motor, respectively. In addition, system controller 178 is electrically connected as indicated by line 196 to colorimeter 164, and as indicated by line 198 to reagent and/or substrate liquids supply and dispensing means drive motor(s) 177; and it will thus be immediately clear to those skilled in this art that the respective automated operations and cycle times of the heretofore described components of the sample liquids analysis system 10 can be very precisely determine coordinated, synchronized and controlled as required by system programmer 178 through the appropriate programming thereof in accordance with the specific requirements and parameters of the analyses to be performed on the sample liquids 36 by the system 10.

Referring again to active probe means component 112 of FIG. 3, and realizing that dimensions may vary in accordance with the requirements of particular sample liquid analysis applications to which the sample liquids analysis system 10 may be put, it may be understood that, for representative system applications wherein volumes of sample liquids 36 of 20 ul are to be withdrawn in turn from successively presented sample liquid receptacles 30 by probe means 22 for dispensing in turn into reaction cuvettes 156 of sample liquid reaction and analysis means 26 for successive, automated sample liquids analyses, active probe component 112 could be of approximately 2.6 inches in overall length, with upper probe component body portion 116 being of approximately 2.0 inches in length, and lower probe component body portion 120 being of approximately 0.6 inches in length, as measured in each instance from approximately the middle of the necked down probe component portion 118. Under these conditions, and with upper probe component body portion 116 being of approximately 0.06 inches in inner diameter, and lower probe component body portion 120 being of approximately 0.02 inches in diameter, volumes of approximately 75ul and 5 ul will be provided for the upper and lower probe component body portions 116 and 120, respectively. These representative dimensions will, in any event, provide probe means 22 with the capability of effectively and precisely aspirating and dispensing successive sample liquids 36 of volume ranging from as small as 1 ul to as large as 75 ul, as described in detail hereinbelow, while insuring with regard to the larger of those sample liquid volumes that no sample liquid 36 ever comes into contact with the somewhat irregular, and thus sample liquid carryover intensive in terms of retention of sample liquid residue, juncture between upper probe component body member portion 116 and rinse liquid supply conduit 94.

Figure 5:
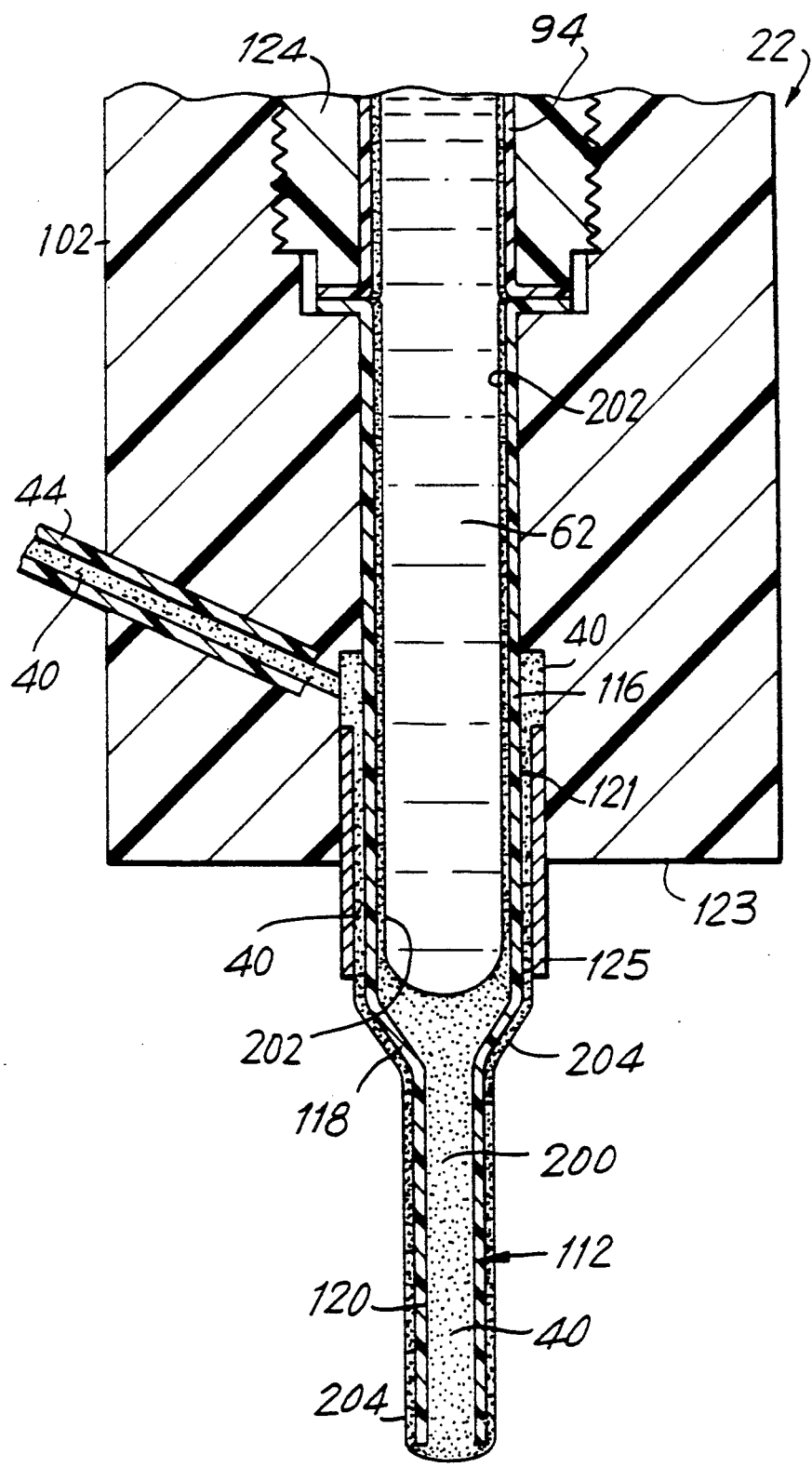
FIGS. 5, 6, 7 and 8 are respectively cross-sectional views in the nature of FIG. 3 illustrating the respective operational configurations of the sample liquid aspirating and dispensing probe means at various stages in the operation of the sample liquids analysis system of FIG. 1.

For a representative sample liquids analysis system application of this nature, and referring now to FIG. 5 of the drawings which depicts the probe means 22 immediately upon the withdrawal thereof from the isolation liquid reservoir means 16 at the completion of a sample liquid aspiration, dispensing and active probe means component cleansing cycle, the active probe component 112 and connected rinse liquid supply conduit 94 will be seen to be substantially filled with rinse liquid 62, supplied thereto from rinse liquid reservoir 60 as described in detail hereinbelow, followed by a segment 200 of the isolation liquid 40 as aspirated by the probe means from the isolation liquid reservoir 50, again as described in detail hereinbelow. In addition, the inner wall of the active probe means component 112 above the isolation liquid segment 200, extending upwardly therein at least to the juncture thereof with the rinse liquid supply conduit 94 if not higher as depicted, is coated with a thin layer 202 of the isolation liquid 40 (shown as of exaggerate thickness in FIG. 5 for purposes of clarity of illustration) which remains therein from previously aspirated isolation liquid 40; while the external wall of the probe component body portions 116 and 120 which extend downwardly below the upper end of annulus 121 are also coated with a thin layer 204 of the isolation liquid 40 (again shown as of exaggerate thickness as above) which flows downwardly thereover from the annulus 121 under the force of gravity, also as described in detail hereinbelow.

At this point in the operation of probe means 22, rinse liquid supply valve 84 has been rotated to the "closed" position thereof; and it may be understood that the combination of atmospheric pressure, and capillary action in the probe component body member 114 as a result of liquid surface tension, will be sufficient to retain the rinse liquid 62 and the isolation liquid segment 200 in the probe component body member 114 to prevent the flow thereof from the same under the force of gravity due to the rinse and isolation liquid "head" in the probe component body member 114 and rise liquid supply conduit 94, respectively. For operation with sample liquids volumes of 20 ul as discussed hereinabove, it may be understood that a representative volume for isolation liquid segment 200 would be 10 ul.

With the probe means 22 removed from the isolation liquid reservoir 50 to expose the open probe tip 122 to the ambient air, and with rinse liquid supply valve 84 remaining closed, it may be understood that sample liquid supply pump 168 is operated by downward movement of pump piston 174 to aspirate a segment 206 of representative volume of 3 ul of ambient air into probe component 112; and this is followed by the indexing of the probe means 22 and the immersion of the open probe tip 122 in the buffer-diluent liquid 102 in container 100, and the continued operation of sample liquid supply pump 168 as describe to aspirate a segment 208 of the buffer-diluent liquid 102 into the probe component; it being clear that, although immersion of the open probe tip 122 in any liquid for aspiration of necessity includes the immersion of some portion of lower probe component body member portion 120 therein, such immersion is strictly limited to that lower probe component body member portion. A representative volume for buffer-diluent liquid segment 208 is 10 ul.

Figure 6:
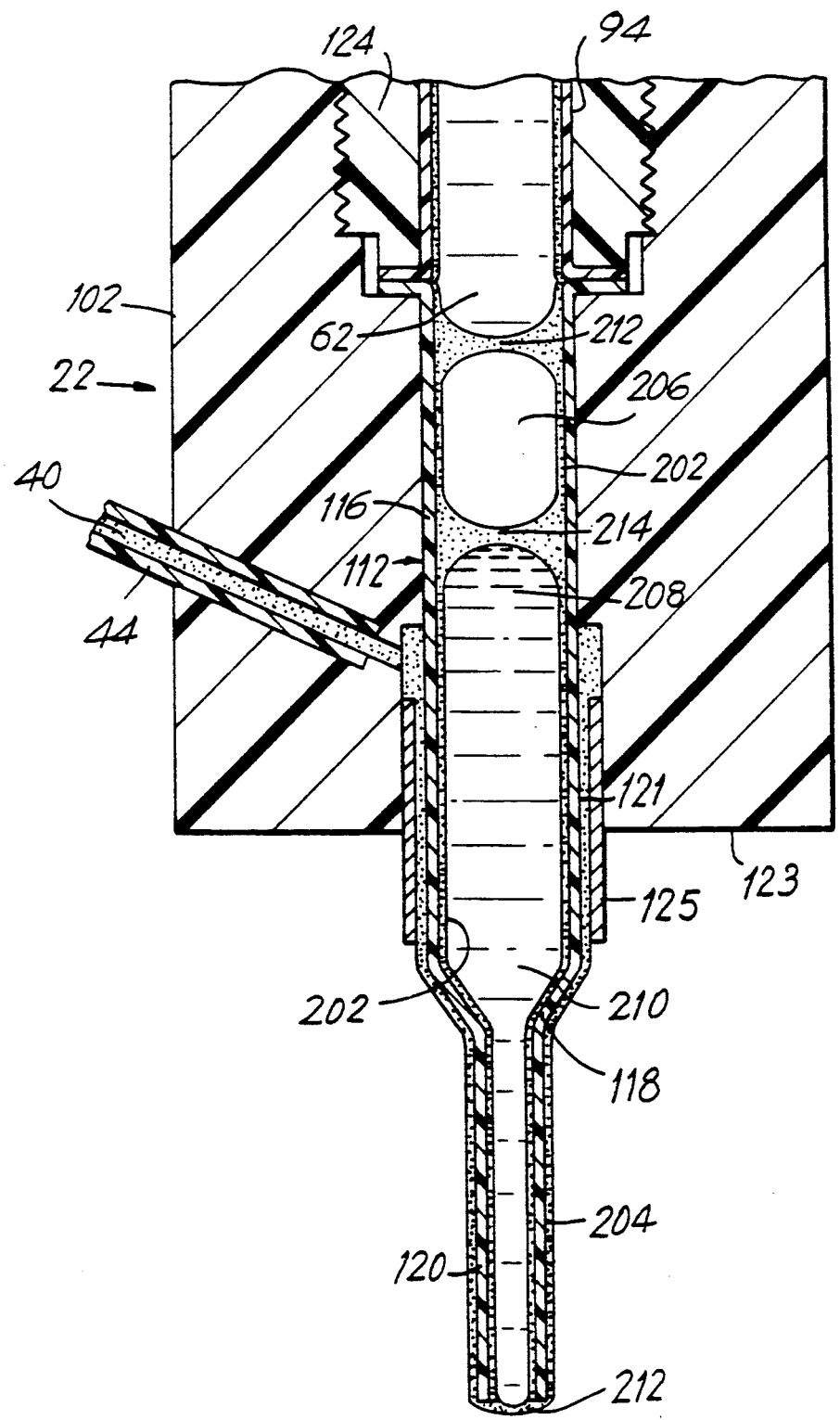

Operation of pump 168 is then discontinued, and the probe means 22 indexed to immerse the open probe tip 122 in the sample liquid 36 in the sample liquid receptacle 30 newly indexed by the shuttle means 32 to the probe means sample liquid off-take station; whereupon sample liquid supply pump 168 is re-activated as described to aspirate a sample liquid segment 210 of 20 ul volume into the probe component 112 for merger therewithin with the buffer-diluent liquid segment 208, as shown in FIG. 6, followed by discontinuance of the operation of the operation of pump 168 and withdrawal of the probe means 22 from the sample liquid receptacle 30.

FIG. 6, which depicts the operational configuration of the probe means 22 at this point in the operation of sample liquids analysis system 10 makes clear that aspiration as described of the respective air, buffer-diluent liquid and sample liquid segments 206, 208 and 210 will displace much of the previously aspirated isolation liquid segment 200 to the inner walls of the probe component 112, with only thin isolation liquid segments as indicated at 212 and 214 (again shown as of exaggerate thickness) remaining between the rinse liquid 62, the air segment 206, and the merged buffer-diluent and sample liquid segments 208 and 210 to separate the same. FIG. 6 also makes clear that the continued flow of the isolation liquid layer 204 downwardly along the outer wall of the relevant portion of active probe component 112 under the force of gravity as described will, in accordance with the natural flow characteristics of that highly viscous liquid, operate to cover the trailing, insofar as order of aspiration is concerned, edge of the merged buffer-diluent and sample liquids segments 208 and 210 with a thin layer (again of exaggerated thickness) 212 of the isolation liquid, thereby making clear that the merged buffer-diluent and sample liquids segments 208 and 210 are effectively encapsulated in the isolation liquid 40.

Figure 7:
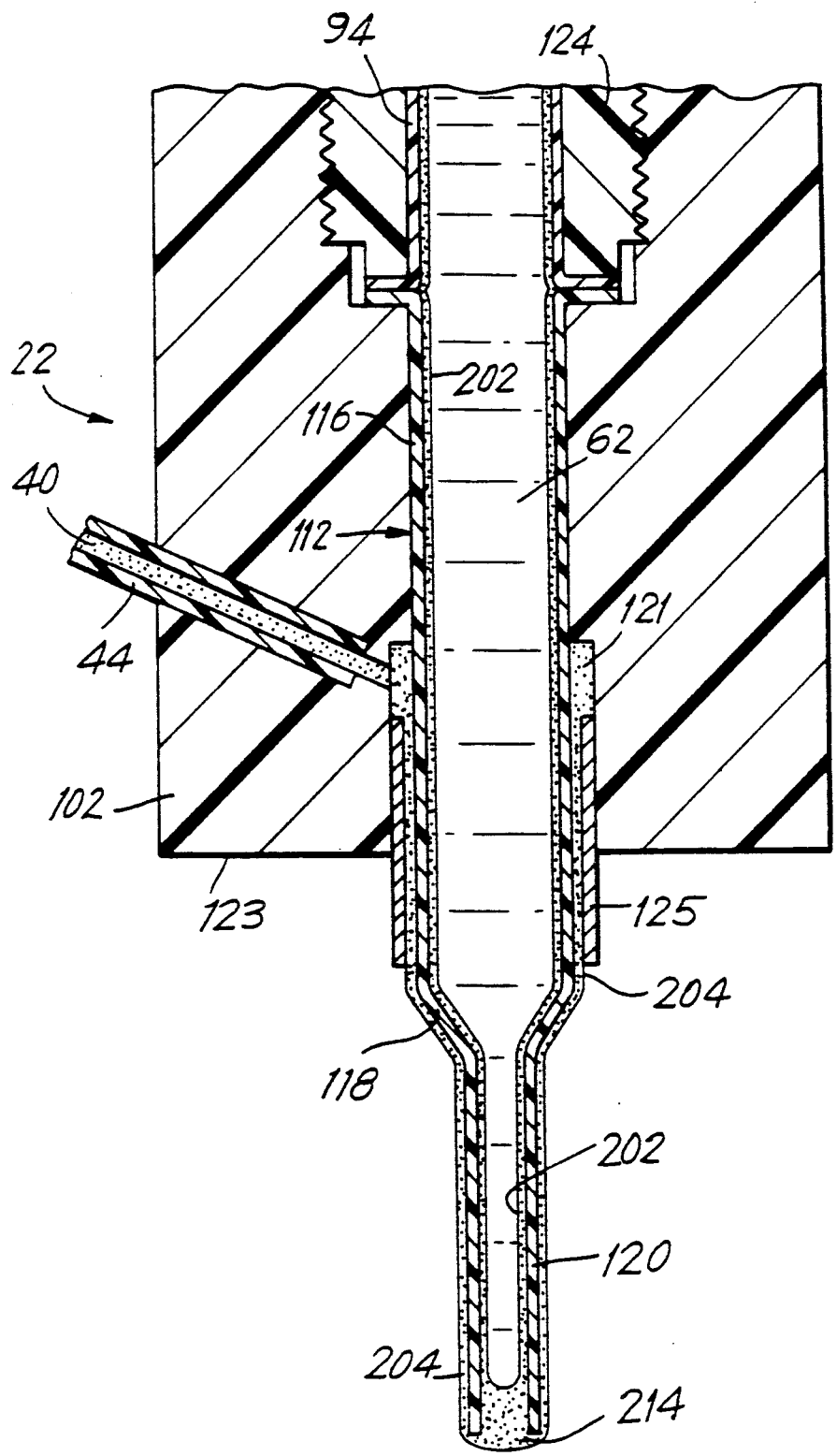

With the probe means 22 in the operational configuration of FIG. 6, the same is then indexed to the probe dispensing station immediately above the next available reaction cuvette 156 as has been indexed as described to that station by rotation of tray 154; and, with rinse liquid supply valve 84 remaining closed sample liquid supply pump 168 is operated by upward movement of pump piston 168 to a precisely predetermined extent to pump all of the isolation liquid-encapsulated, merged buffer-diluent and sample liquid segments 208 and 210 from the probe component 112 into the cuvette 156 through open probe tip 122, thereby leaving the probe means 22 essentially in the operational configuration illustrated in FIG. 7 wherein the probe component 112 is again substantially filled with the rinse liquid 62, with some measure of the isolation liquid 40 remaining at the probe tip 122 as indicated at 214, and the isolation liquid layers 202 and 204 at the respective outer and inner walls of the active probe component 112 remaining intact, both as also made clear by FIG. 7. A representative volume of the isolation liquid dispensed as described by the probe means 22 into the cuvette 156 with the merged buffer-diluent and sample liquid segments 208 and 210 is 2 ul, with much of the isolation liquid remaining in the active probe means component 112 having been further displaced to the inner walls thereof attendant buffer-diluent and sample liquid dispensing therefrom as described.

The addition of the requisite reagent(s) and/or substrate(s) liquids to the thusly dispensed sample liquid 36 in the reaction cuvette 156 by the supply means 28 for those liquids as heretofore described through appropriate indexing of the reaction tray 154, the further treatment of the same as may be required in the reaction cuvette 156, and the analysis of the thusly reacted and treated sample liquids 165 (FIG. 1) by the optical sample liquids analysis means 164 are then automatically accomplished.

Following sample liquid dispensing as described into the reaction cuvette for analysis, probe means 22 are indexed to the position thereof immediately over the isolation liquid reservoir 50 (FIG. 1), and at least that part of the lower probe member body portion 112 which was immersed as heretofore described in the sample liquid container 30 is immersed in the isolation liquid 40 in that reservoir; whereupon rinse liquid supply valve 84 is opened, and rinse liquid supply pump 76 activated to pump the isolation liquid quantity 214 (FIG. 7), the rinse liquid 62 then present in the active probe component 112 and in rinse liquid supply conduit 94, plus an appropriate quantity of the rinse liquid from rinse liquid supply container 62 to and through the probe means component 112 as the case may be out of the open probe component tip 122 into the reservoir 50 against the direction of aspirated sample liquid flow in the active probe component 112. This very effectively back-flushes the interior wall of the probe component 112, virtually insuring the removal of all residue of the just-dispensed sample sample liquid 36 therefrom; with the thusly pumped rinse liquid, which is of lower specific gravity than the isolation liquid, simply flowing from the probe component 112 into the isolation liquid 40 in the reservoir 50, and rising to the top of the latter for flow as indicated as the rinse liquid layer 53 atop the isolation liquid 40 from reservoir 50 through overflow chamber 52 to waste via drain conduit 54 as seen in FIG. 1. A representative volume of rinse liquid 40 which is pumped as described from active probe component 112 during this rinsing cycle is 300 ul.

Rinse liquid supply valve 84 is then closed, and sample supply pump 168 activated to aspirate the 10 ul segment 200 of the isolation liquid 40 into the probe component 112 through open probe tip 122 from the isolation liquid reservoir 50; and the probe component 112 then removed from the isolation liquid reservoir 50 to assume the operational configuration thereof of FIG. 5 for repetition of the sample liquid aspiration and dispensing cycle as described; with a further coating of the isolation liquid having been added to the relevant portion of isolation liquid layer 204 at the exterior wall of the active probe component 112 by the immersion thereof in the same in the isolation liquid reservoir 50 as described.

Replenishment of the supply of the isolation liquid 40 in the isolation liquid reservoir 50, and of the supply thereof to probe body member—active probe component annulus 121 (FIG. 1 both to insure that there is always sufficient isolation liquid in the reservoir 50 to enable the aspiration as described by the probe means 22 of the isolation liquid segment 200 prior to buffer-diluent and sample liquids segments aspirations as described, and to insure the continued presence of the isolation liquid layers 202 and 204 on the respective interior and exterior walls of the active probe means component 112 attendant all operations of the probe means 22, is provided by the periodic operations of peristaltic pumps 46 and 48 to supply the isolation liquid 40 via conduits 42 and 44 as heretofore described. These periodic operations of pumps 46 and 48 may, for example, occur immediately prior to sample liquid aspiration and immediately following sample liquid dispensing, respectively; and a representative volume of the isolation liquid 40 thusly supplied per sample liquid aspiration and dispensing cycle of the probe means 22 is 20 ul.

Figure 8:
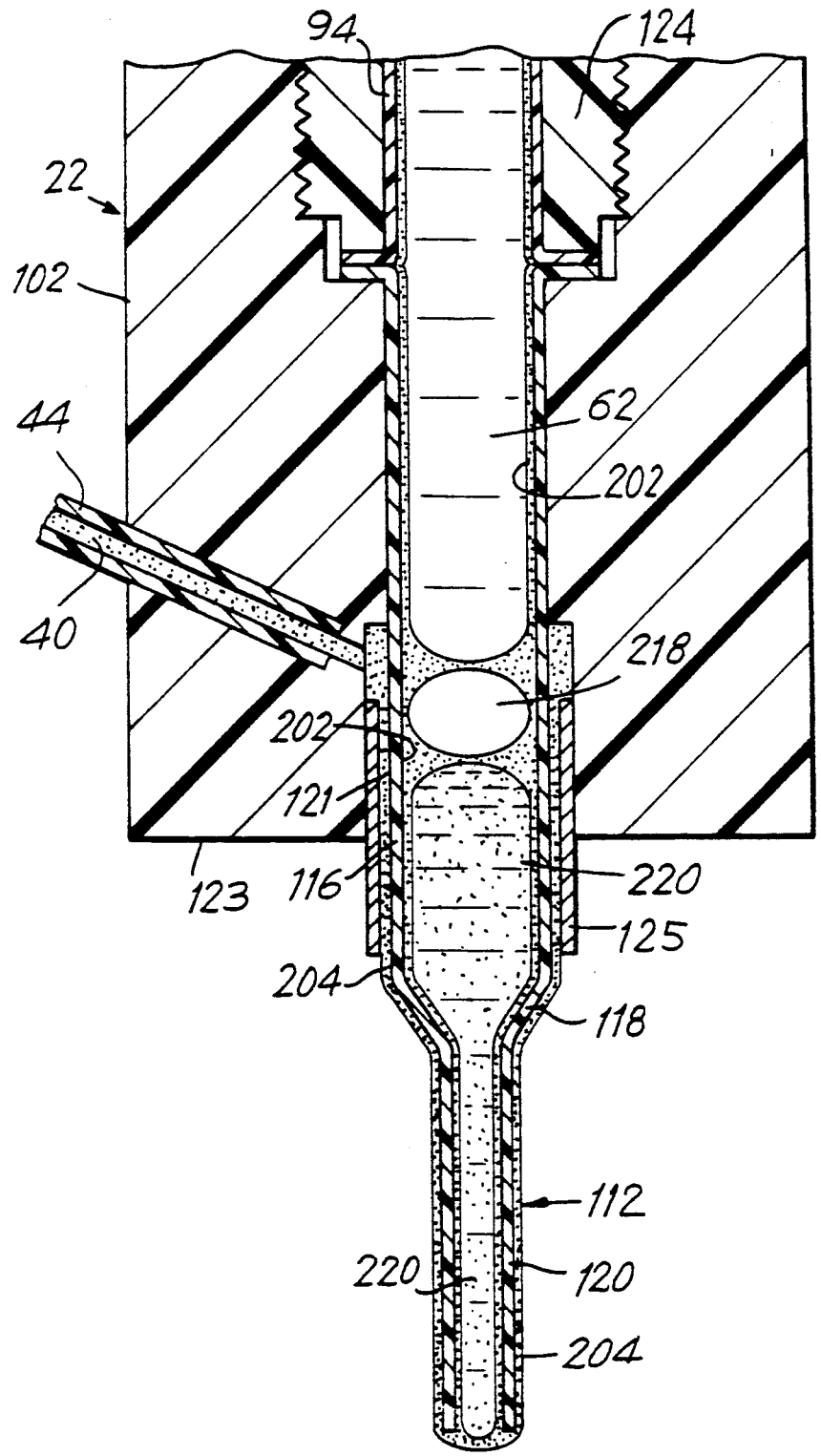

For use, for representative example, of the sample liquids analysis system 10 in the automated performance of heterogeneous immunoassays on human blood sera for determination of the presence of the pregnancy hormone Beta HCG therein, and which require the addition of the magnetic particles 152 (FIG. 1 to the sample and reagent liquids in the reaction cuvette, all as described in some detail with regard to methodology in co-pending application for U.S. Pat. application Ser. No. 07/384,594 filed concomitantly herewith by Berri Cohen, et al, for "Automated Analytical Apparatus And Method," and assigned to the assignee hereof, it may be understood that immersion of the active probe means component 112 in the isolation liquid reservoir 50 as heretofore described following dispensing of a sample liquid 36 into a reaction cuvette 156 would, in turn, be followed only by the pumping of the rinse liquid 62 from reservoir 60 through the probe component 112 against the direction of aspirated sample liquids flow to thoroughly back-flush and rinse the same; whereupon the probe means 22 would be removed from the isolation liquid reservoir 50 without the aspiration of the isolation liquid segment 200, thus leaving the probe means component 112 filled with rinse liquid 62, with rinse liquid supply valve 84 closed. Sample liquid supply pump 168 is then operated to aspirate a segment 218 of ambient air of representative 3 ul volume through the open probe tip 122 into probe component 112; and this is followed by immersion of the probe component 112 as heretofore described into the liquid-suspended magnetic particles 152 in supply container 150 for the aspiration, again through operation of sample liquid supply pump 168, of a segment 220 of the liquid-suspended magnetic particles 152 thereinto in a representative volume of 20 ul. The operational configuration of the probe means 22 at this stage in the sample liquids analysis process is depicted in FIG. 8.

Following the above, the probe means 22 are indexed to immerse the probe component 122 in a previously dispensed sample liquid 36 in a reaction cuvette 156 to which the requisite reagent liquid(s) have already been added as indicated at 165 in FIG. 1, and the sample liquid supply pump 168 again operated to dispense the liquid suspended magnetic particles segment 220 thereinto for mixture with the appropriately reacted sample liquid; and it will be readily understood by those skilled in this art that, in order to insure that the sample-reagent(s) liquids reaction has proceeded as required to completion in the cuvette 156 of interest prior to the introduction of the liquid-suspended magnetic particles segment 200 thereto, a not insubstantial time period, for representative example 20 minutes, may have elapsed between the time that the sample and reagent(s) liquids were introduced to the reaction cuvette 156, and the time at which the liquid-suspended magnetic particles segment 220 is introduced thereinto. In accordance with the teachings of the invention, the probe means 22 and the sample liquids reaction and analysis means 26 do not remain idle during this time period; but rather, and in accordance with the full random access capabilities of the sample liquids analysis system 10 as set forth in some detail in U.S. Pat. No. 4,629,703 incorporated by reference in this specification hereinabove, remain operational at full capacity to aspirate, dispense, react, treat and analyze other and different sample liquids as heretofore described.

Following liquid-suspended magnetic particles dispensing as described, the now again rinse liquid-filled probe means 22 are indexed from the reaction cuvette 156 of interest and returned for immersion of the probe means component 122 to the isolation liquid reservoir 50 for repetition of the probe means rinse cycle as heretofore described, and the withdrawal of the probe component 122 therefrom, either with or without the isolation liquid segment 200 of FIG. 5 depending upon the next application to which the probe means 22 are to be put, namely sample liquid or liquid-suspended magnetic particles aspiration.

Although the number of sample liquids analyses that can be accomplished by the sample liquids analysis system 10 can vary in accordance with the particular requirements of the same, a representative operational rate for the system 10 is 120 of such sample liquids analyses per hour; with a representative cycle time for the probe means 22 between successive sample liquids aspirations being approximately 3 seconds.

In addition to the significant advantages with regard to reduction of sample liquid carryover provided as heretofore described by the isolation liquid layers 204 and 202 on the exterior and interior walls of the active probe means component 112, which advantages are by now well known and understood by those skilled in this art, it will be clear that the sample liquids analysis system 10 of the invention provides the additionally significant advantages, again with regard to reduction of sample liquid carryover, of very thorough rinse of the same; it having been determined that, under certain sample liquids analysis conditions, sample liquids residues, for example in the form of protein molecules as present in human blood sera, which are extremely "sticky," can and do adhere to the isolation liquid layers at the exterior and interior walls (primarily the latter) of the active probe component; and, that in the absence of rinse thereof, can and do contribute to measurable sample liquid carryover, albeit at very low levels. Forceful rinsing as described of the isolation liquid layer 202 at the interior wall of the active probe component 112 by the rinse liquid in the direction opposite to the direction of aspirated sample liquid flow to back-flush the same has proven effective to remove virtually all of any such sample liquid residue as may be present thereon; while the forceful immersion of the relevant portion of the active probe means component 112 into and through the rinse liquid layer 53 (FIG. 1) and isolation liquid 40 in the isolation liquid reservoir 50, and the subsequent forceful withdrawal of that probe means component portion therethrough following rinse liquid flow as described, have proven effective to remove virtually all of any such sample liquid residue as may be present on the isolation liquid layer 204 on the exterior wall of that relevant probe means component portion. Too, the virtually constant presence of the rinse liquid 40 in the active probe means component 112, both prior and subsequent to sample liquid aspiration and dispensing as described, of course tends to further cleanse the isolation liquid layer 202 at the relevant interior probe component wall portion by picking up sample liquid residue, if any, therefrom for expulsion from the probe component 112 with the rinse liquid into the isolation liquid reservoir 50 during the probe component rinse cycle.

Additional minimization of sample liquid carryover is provided in the sample liquids analysis system 10 by the aspiration of the buffer-diluent liquid segment 208 which, for the aspiration of sample liquid segments 210 of volume warranting the same, for example 10 ul or above, contains a reasonably high concentration, for example 20% by volume, of an appropriate surfactant as heretofore described; it being understood that the thusly constituted buffer-diluent liquids segment 208, which merges as heretofore described with regard to FIG. 6 with the subsequently aspirated sample liquid segment 210 to place the highest buffer-diluent liquid concentration at the back or upper end of the thusly merged liquids segment, operates to very significantly reduce the overall surface tension of that merged liquids segment, in particular at the more critical back or upper end thereof, thereby better retaining the physical integrity thereof and providing a far more cohesive merged essentially aqueous liquids segment 208 and 210 in the adjacent presence of the isolation liquid 40 for expulsion as such, essentially without merged liquids segment break-up and attendant "loose" sample liquid residue, from the active probe means component 112 upon segment dispensing as heretofore described into a reaction cuvette 156. In addition, the presence of the surfactant in the buffer-diluent liquid segment 208 functions to materially increase the mobility of the ordinarily not particularly mobile protein molecules as may be present in the sample liquid segment 210, and this greatly reduces the nonspecific binding characteristics of those protein molecules, and the likelihood of the same adhering to the isolation liquid layer 202.

In accordance with all of the above, and for use for example in the automated performance of heterogeneous immunoassays on human blood sera samples with regard to the pregnancy hormone Beta HCG as discussed hereinabove, it may be understood that the sample liquids analysis system 10 of the invention has proven effective in tests to date to consistently meet, or even exceed, the ultra low sample liquid carryover limit of 5 parts per million of succeeding sample liquid as required for the validity of the same; and it will be immediately clear to those skilled in this art that no known automated sample liquids analysis system which relies on isolation liquid alone for sample liquid carryover minimization can consistently meet that particularly stringent standard.

With regard to the probe means 22 of the invention, per se, the same will immediately be seen to also offer the particularly significant advantage of providing for the simple, low cost, and virtually immediate replacement of the active probe means component 112 in the event of physical damage thereto as does occasionally occur due, for example to operator error in the operation of an automated sample liquids analysis system, with minimal analysis system down-time, and virtually no adverse effect upon the requisite fine degree of system calibration, and/or the accuracy of subsequent system operation. More specifically, and in the event of damage to active probe means component 112 requiring the replacement thereof, the system 10 is shot down, hex nut 124 is simply unscrewed and removed from probe means body member 102 without adverse effect of any nature upon rinse liquid supply conduit 94 which simply remains inserted therein as heretofore shown and described, the damaged active probe means component 112 simply removed from probe means body member 102 by pushing the same upwardly from the component bottom until the flared component end 142 can be freely grasped by the fingers or appropriate tool within the probe body member bore 104 for simple removal of the component 112 therefrom, a "new" probe means component 112 simply inserted from the top into the body member bore 103 and pushed therethrough until the flared component end 142 comes to rest on bore surface 144, and the hex nut 124, with the rinse liquid supply conduit 94 remaining operatively disposed therein, and absolutely unchanged with regard to length, configuration, and particular liquid flow characteristics, simply re-inserted into body member bore 104 and screwed tightly thereinto to re-establish the fluid-tight connection between the flared ends 140 and 142 of the rinse liquid supply conduit 94 and the "new" active probe means component 112, and the requisite communication between the same. This makes clear that re-placement of the active probe means component 112 can be readily and conveniently accomplished as described totally without adverse effect upon what is generally termed the "service loop," i.e. the relevant lengths of rinse liquid supply conduit 94 and isolation liquid supply conduit 44, and thus upon the accuracy of subsequent analysis system performance; with the cost of such replacement beyond time costs being limited to the cost of the "new" active probe means component 112 which is, of course, decidedly minimal, and no time-consuming fine re-calibration of the sample liquids analysis system 10 required. In accordance with the above, it should be immediately clear to those skilled in this art that no prior art probe means suitable for use in highly sophisticated automated sample liquids analysis systems of the type here under discussion can meet these highly demanding requirements of ease, low cost, minimal system down-time and virtually non-existent adverse impact upon subsequent system performance with regard to effective probe means replacement.

Various changes can of course be made be made in the invention as disclosed herein without departing from the spirit and scope thereof as defined in the appended claims.

What is claimed is:

1. A sample liquid probe for the aspiration of sample liquids in turn from a plurality of distinct sample liquid containers, said sample liquid probe comprising a probe body member, an active probe component having an inlet end and being operatively disposed in said probe body member, said active probe component extending from aid probe body member beyond the same, a conduit extending from said probe body member beyond the same, connecting means operatively associated with said probe body member said active probe component, and said conduit, said connecting means and said probe body member comprising co-operable attachment means for attaching said connecting means to said probe body member to directly connect said conduit to said active probe component in abutting liquid-tight manner within said probe body member to establish direct, liquid-tight manner within said probe body member to establish direct, liquid-flow communication between said conduit and aid active probe component within said probe body member, and automatically operable probe drive means operatively connected to said probe body member for automatically moving said probe body member relative to said distinct sample liquid containers to immerse the inlet end of said active probe component in turn in said distinct sample liquid containers for the aspiration of sample liquids therefrom into said active probe component through said inlet end.

2. A sample liquid probe as in claim 1 further comprising, said active probe component comprising a generally vertically oriented tubular body member having an upper body member portion and a lower body member portion, with said upper body member portion being of greater diameter than said lower body member portion and transitioning smoothly thereinto.

3. A sample liquid probe as in claim 1 further comprising, said connection between said conduit and said active probe component being readily disconnectable, whereby replacement of said active probe component may be readily accomplished by the removal of said connecting means from said probe body member and the disconnection of said active probe component from said conduit without adverse effect on said conduit.

4. A sample liquid probe as in claim 1 further comprising, said sample liquid probe being a sample liquid aspirating and dispensing probe, said conduit being a rinse liquid supply conduit, and means operatively associated with said conduit for automatically aspirating sample liquids into said active probe component in turn from said distinct sample liquid containers, for automatically dispensing the thusly aspirated sample liquids in turn from said active probe component, and for automatically flowing a rinse liquid into and through said active probe component following the dispensing of each of said sample liquids therefrom to rinse sample liquid residue therefrom and minimize sample liquid carryover upon the aspiration of a succeeding sample liquid into said active probe component.

5. A sample liquid probe as in claim 4 further comprising, means operatively associated with said active probe component and operable to supply an isolation liquid thereto to form isolation liquid layers on the interior and exterior walls of said active probe component, said isolation liquid being immiscible with said sample liquids and aid rinse liquid, and being operable to preferentially wet the interior and exterior walls of said active probe component to the substantial exclusion of said sample and rinse liquids whereby, the adherence of sample liquid residue to those walls is inhibited.

6. A sample liquid probe as in claim 5 further comprising, said active probe component being made of a hydrophobic material.

7. A sample liquid probe as in claim 6 further comprising, said probe body member being made of a hydrophobic material.

8. A sample liquid probe as in claim 1 further comprising, said conduit being readily flexible, whereby minimal interference to the movement of said probe body member by said probe drive means will be presented by said conduit.

9. A sample liquid probe as in claim 1 further comprising, said conduit and said active probe component being generally tubular and comprising flared ends of essentially like diameter, said probe body member and said connecting means respectively comprising means operable upon the attachment of the same by said attachment means to firmly press said flared conduit and active probe component ends together in liquid-tight manner to directly connect said conduit to said active probe component.

* * * * *